US010064837B1

United States Patent
Amr et al.

(10) Patent No.: US 10,064,837 B1
(45) Date of Patent: Sep. 4, 2018

(54) ABIETIC ACID DERIVATIVES AS ANTI-TUMOR AGENTS

(71) Applicant: KING SAUD UNIVERSITY, Riyadh (SA)

(72) Inventors: Abd El-Galil E. Amr, Riyadh (SA); Mohamed A. Al-Omar, Riyadh (SA); Abdulrahman A. Almehizia, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/897,912

(22) Filed: Feb. 15, 2018

(51) Int. Cl.
| | |
|---|---|
| *A61K 31/216* | (2006.01) |
| *A61K 31/265* | (2006.01) |
| *A61K 31/365* | (2006.01) |
| *A61P 35/00* | (2006.01) |
| *A61K 31/167* | (2006.01) |

(52) U.S. Cl.
CPC .......... *A61K 31/265* (2013.01); *A61K 31/167* (2013.01); *A61K 31/216* (2013.01); *A61K 31/365* (2013.01); *A61P 35/00* (2018.01)

(58) Field of Classification Search
CPC ... C07C 69/757; C07C 327/00; C07C 235/40; C07C 2603/26; A61K 31/216; A61K 31/265; A61K 31/365
See application file for complete search history.

(56) References Cited

U.S. PATENT DOCUMENTS

| 5,248,696 A | 9/1993 | Bang et al. |
|---|---|---|
| 7,015,248 B2 | 3/2006 | Lin et al. |
| 2010/0022632 A1 | 2/2010 | Hsiao et al. |
| 2012/0141578 A1 | 6/2012 | Robertson et al. |
| 2016/0002279 A1 | 1/2016 | Li et al. |

FOREIGN PATENT DOCUMENTS

| KR | 10-0841068 B1 | 6/2008 |
|---|---|---|
| KR | 10-0882780 B1 | 2/2009 |

OTHER PUBLICATIONS

Kutney et al, Helvetica Chimica Acta, 66. Studies Related to Biological Detoxification of Kraft Pulp Mill Effluent. III.The Biodegradation of Abietic Acid with Mortierella isabellina, 1982, 65(3), pp. 661-670. (Year: 1982).*
Huang, Xiao-Chao et al., "Synthesis and antitumor activities of novel dipeptide derivatives derived from dehydroabietic acid", Bioorganic & Medicinal Chemistry Letters, vol. 24, pp. 1511-1518, 2014.
Gonzales, Miguel A. et al., "Synthesis and biological evaluation of dehydroabietic acid derivatives", European Journal of Medicinal Chemistry, vol. 45, pp. 811-816, 2010.
Roh, Seong-Soo et al., "Abietic Acid from Resina Pini of Pinus Species as a Testosterone 5α-Reductase Inhibitor", Journal of Health Science, vol. 56(4), pp. 451-455, 2010.
Iwal, Atsushi et al., "Spectrophotometric Method for the Assay of Steroid 5α-Reductase Activity of Rat Liver and Prostate Microsomes", Analytical Sciences, vol. 29, pp. 455-459, 2013.
Shiraishi, Steve et al., "Simultaneous Measurement of Serum Testosterone and Dihydrotestosterone by Liquid Chromatography-Tandem mass Spectrometry", Clinical Chemistry, vol. 54:11, pp. 1855-1863, 2008.

* cited by examiner

*Primary Examiner* — Paul A Zucker
(74) *Attorney, Agent, or Firm* — Richard C. Litman (57) ABSTRACT

The abietic acid derivatives as anti-tumor agents are derivatives of abietic acid in which the hydroxyl entity (—OH) of the carboxyl entity is replaced by an electronegative substituent, which may be C6H5-O—, C6H5-S—, or C6H5-NH—, and a hydrogen atom on one of the rings is replaced by a hydroxyl (—OH) substituents, the derivatives having the formula:

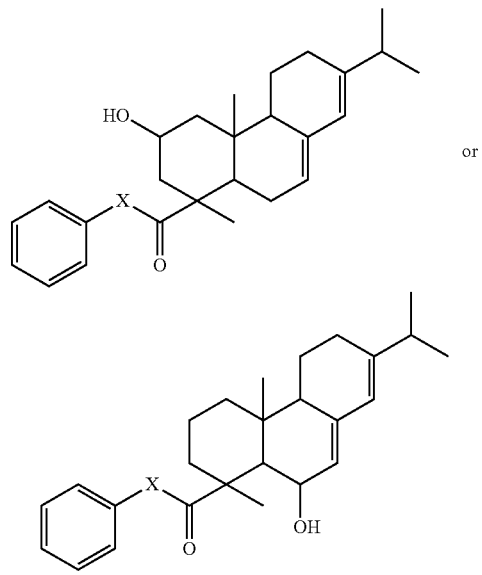

wherein X is O, S, or NH. The derivatives are formed by formation of an intermediate lactone from abietic acid, followed by reaction of the lactone with phenol, thiophenol, or aniline. All of the derivatives exhibited potent 5α-reductase inhibitor activity, both in vitro and in vivo, and anti-tumor activity with regard to two prostate cancer cell lines—LNCaP and PC-3. The intermediate lactones are also derivatives of abietic acid that exhibit anti-tumor activity.

13 Claims, 3 Drawing Sheets

ABIETIC ACID DERIVATIVES AS ANTI-TUMOR AGENTS

BACKGROUND

1. Field

The disclosure of the present patent application relates to anti-tumor agents derived from natural products, and particularly to abietic acid derivatives as anti-tumor agents shown to have anti-cancer activity against two prostate cancer cell lines.

2. Description of the Related Art

Cancer is a deadly disease that knows no geographic boundaries. Currently the primary treatment modalities continue to be radiation, chemotherapy, and surgery. However, each of these treatment modes is frequently accompanied by harsh side effects. As a consequence, much modern medical research has been directed to the chemistry of natural products that have been reported to exhibit anticancer activity, either in folk medicine or in isolated laboratory studies.

The terpenes are a large family of natural products commonly obtained from plant and fungal sources. Many terpenes have been found to provide medicinal activity, including activity that suggests their use as anti-tumor agents.

Abietic acid is a tricyclic diterpenoidal acidic resin available from plant sources (from *Pinus* spp.), having the following structure:

Abietic acid has a cytotoxic effect. It inhibits gastric acid secretion, and as a result, has use as an antiulcer agent. Abietic acid also has been shown to demonstrate anti-inflammatory, antimicrobial, and anticonvulsant activity. Further, abietic acid and certain abietic acid derivatives have demonstrated anti-tumor activity against some forms of cancer. Prostate cancer is a severe form of cancer that often goes undiagnosed until it is too late for effective treatment. Nevertheless, it would be of interest to develop a derivative of abietic acid that can be shown to exhibit anti-tumor activity against prostate cancer.

In the description that follows, the nomenclature of compounds described herein generally follows the IUPAC recommendation, which call for numbering the carbons in abietic acid and its derivatives in accordance with the numbering of abietane, which is as follows:

It will be understood that the numbering of C18 and C19 is interchangeable, as is the numbering of C16 and C17, so that generally whichever numbering is lowest in a particular compound will be selected.

Thus, abietic acid derivatives as anti-tumor agents solving the aforementioned problems are desired.

SUMMARY

The abietic acid derivatives as anti-tumor agents are derivatives of abietic acid in which the hydroxyl entity (—OH) of the carboxyl entity is replaced by an electronegative substituent, which may be C6H5-O—, C6H5-S—, or C6H5-NH—, and a hydrogen atom on one of the rings is replaced by a hydroxyl (—OH) substituents, the derivatives having the formula:

or wherein X is O, S, or NH. The derivatives are formed by formation of an intermediate lactone from abietic acid, followed by reaction of the lactone with phenol, thiophenol, or aniline. All of the derivatives exhibited potent 5α-reductase inhibitor activity, both in vitro and in vivo, and anti-tumor activity with regard to two prostate cancer cell lines—LNCaP and PC-3. The intermediate lactones are also derivatives of abietic acid that exhibit anti-tumor activity.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The abietic acid derivatives as anti-tumor agents are derivatives of abietic acid in which the hydroxyl entity (—OH) of the carboxyl entity is replaced by an electronegative substituent, which may be C6H5-O—, C6H5-S—, or C6H5-NH—, and a hydrogen atom on one of the rings is replaced by a hydroxyl (—OH) substituents, the derivatives having the formula:

wherein X is O, S, or NH. The derivatives are formed by formation of an intermediate lactone from abietic acid, followed by reaction of the lactone with phenol, thiophenol, or aniline. All of the derivatives exhibited potent 5α-reductase inhibitor activity, both in vitro and in vivo, and anti-tumor activity with regard to two prostate cancer cell lines—LNCaP and PC-3. The intermediate lactones are also derivatives of abietic acid that exhibit anti-tumor activity.

Figure 1:
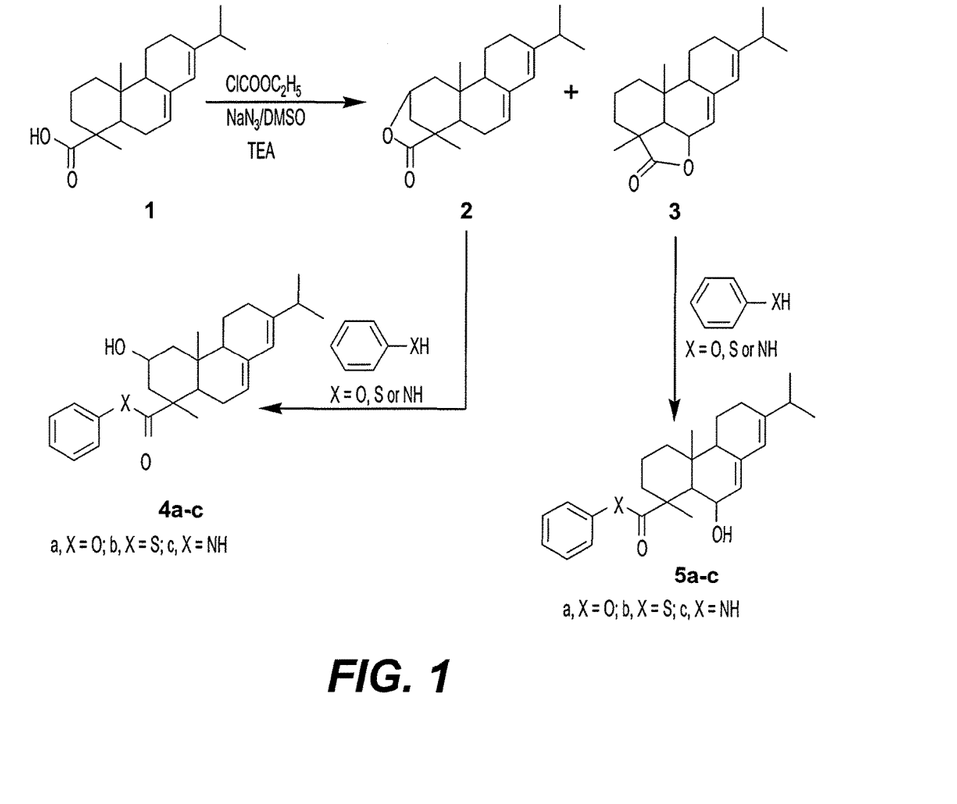
FIG. 1 is the reaction scheme for making the abietic acid derivatives as anti-tumor agents.

The general reaction scheme of the reactions is set forth in FIG. 1. Abietic acid (Compound 1) is treated with ethyl chloroformate and sodium azide in dimethylsulfoxide (DMSO) in the presence of triethylamine (TEA). Two products result, namely, abieta-7,13-dien-18-oic acid (18→2) lactone (compound 2) and abieta-7,13-dien-18-oic acid (18→6) lactone (compound 3). Separation of the two products, compounds 2 and 3, was carried out using medium pressure chromatography. Once separated, each of the two compounds 2 and 3 was subjected to the same further reactions.

Reacting abieta-7,13-dien-18-oic acid (18→2) lactone 2 with phenol, thiophenol or aniline produced the corresponding phenolic ester (compound 4a), thioester (compound 4b), or anilide (compound 4c), respectively, containing the hydroxyl group attached to the C2 position.

Similarly, reacting abieta-7,13-dien-18-oic acid (18→6) lactone 3 with phenol, thiophenol, or aniline) produced the corresponding phenolic ester (compound 5a), thioester (compound 5b), or anilide (compound 5c), respectively (Scheme 1), containing the hydroxyl group attached to the C6 position.

This hydroxyl group in compounds 4a-4c and 5a-5c, whether attached at the C2 or C6 position, apparently plays an important role in increasing anti-tumor activity.

The lactone ring incorporated in intermediate compounds 2 and 3 is thought to serve to increase the negative charge on the molecule, as compared to abietic acid 1. Further, the synthesis of these compounds 2 and 3 to produce compounds 4a to 4c and 5a to 5c opened the lactone ring. The resulting high electronegative hydroxyl and carboxyl groups also seem to help increase both inhibition of 5α-reductase activity and anti-prostate cancer activity.

The following analytical equipment and methods were used to evaluate compounds 2, 3, 4a-4c, and 5a-5c. All melting points were measured using an electrothermal capillary melting point apparatus, and are uncorrected as reported here. The IR spectra were recorded on a Shimadzu FT-IR 8101 PC infrared spectrophotometer. The $^1$H-NMR spectra were determined using a Bruker AM-200 MHz spectrometer. The chemical shifts are expressed on the δ (ppm) scale using tetramethylsilane (TMS) as the standard reference. Mass spectra were recorded on a Thermo Finnigan TSQ mass spectrometer operating at 70 eV. Elemental analysis was conducted on a Perkin Elmer 240 (microanalysis), at the Microanalysis Center, Cairo University, Cairo, Egypt.

Example 1

Synthesis of Intermediate Compounds 2 and 3

As reflected in FIG. 1, a mixture of abietic acid 1 (3.02 gm, 10 mmol) and ethyl chloroformate (1.25 ml, 10 mmol) in 125 ml. of a 1:1 mixture of tetrahydrofuran and dimethylsulfoxide was stirred for one hour in the presence of trimethylamine (0.75 ml, 10 mmol), at room temperature. Sodium azide (0.65 gm, 10 mmol) was added to the reaction mixture, which was then stirred for one hour at room temperature. The reaction mixture was then poured into water, and the resulting precipitate was filtered off, dried and washed with benzene to remove un-reacted starting material. The resulting product mixture was fractionated using a medium pressure chromatography system on a silica gel column using benzene/ethyl acetate (9:1) as solvent, at a pressure of 12 bar and a flow rate of 4 ml/min$^{-1}$, to separate the two lactone compounds 2 and 3.

Example 2

Analysis of Compound 2 (Abieta-7, 13-dien-18-oic acid (18→2) lactone (2))

Yield 42%, mp. 227-229° C., $[\alpha]_D^{25}$=+112 (c 1, MeOH). IR (KBr, cm$^{-1}$): 2988 (CH, aliphatic), 1747 (C=O), 1637, (C=C). $^1$H NMR (DMSO-d$_6$): 0.87 (s, 3H, CH$_3$, C-20), 1.21 (s, 6H, 2CH$_3$, C-16&17), 1.28 (s, 3H, CH$_3$, C-19), 1.36 (t, 2H, CH$_2$, $^1$H), 1.44 (t, 2H, CH$_2$, $^3$H), 1.63 (t, 2H, CH$_2$, $^{11}$H), 1.76 (m, 1H, CH, $^{15}$H), 1.92 (d, CH$_2$, $^2$H, H), 1.96 (t, CH$_2$, 2H, $^{12}$H), 2.0 (t, 1H, CH, $^9$H), 2.52 (t, 1H, CH, $^5$H), 4.28 (m, eq-1H, CH, $^2$H), 5.36 (m, 1H, $^7$H), 5.77 (s, 1H, $^{14}$H). $^{13}$C NMR (DMSO-d$_6$): δ ppm 38.32 (C-1), 65.55 (C-2), 37.23 (C-3), 46.35 (C-4), 44.97 (C-5), 25.67 (C-6), 120.55 (C-7), 135.54 (C-8), 51.00 (C-9), 34.5 (C-10), 22.59 (C-11), 27.56 (C-12), 145.17 (C-13), 122.58 (C-14), 34.89 (C-15), 20.90 (C-16), 21.48 (C-17), 183.77 (C-18), 16.73 (C-19), 14.0 (C-20). MS (EI): m/z 300 (100%) [M$^+$]. Anal. Calculated for C$_{20}$H$_{28}$O$_2$ (300.43): Calculated C, 79.96; H, 9.39. Found C, 79.90; H, 9.35.

Example 3

Analysis of Compound 3 (Abieta-7,13-dien-18-oic acid (18→6) lactone (3))

Yield 41%, mp. 301-303° C., [α]$_D^{25}$=+88 (c 1, MeOH). IR (KBr, cm$^{-1}$): 2981 (CH, aliphatic), 1751 (C=O), 1648, (C=C). $^1$H NMR (DMSO-d$_6$): 0.89 (s, 3H, CH$_3$, C-20), 1.23 (s, 6H, 2CH$_3$, C-16&17), 1.26 (m, 2H, CH$_2$, $^2$H), 1.30 (s, 3H, CH$_3$, C-19), 1.39 (t, 2H, CH$_2$, $^1$H), 1.48 (t, 2H, CH$_2$, $^3$H), 1.67 (t, 2H, CH$_2$, $^{11}$H), 1.79 (m, 1H, CH, $^{15}$H), 1.98 (t, CH$_2$, 2H, $^{12}$H), 2.04 (t, 1H, CH, $^9$H), 2.54 (t, 1H, CH, $^5$H), 4.31 (m, eq-1H, CH, $^6$H), 5.40 (m, 1H, $^7$H), 5.83 (s, 1H, $^{14}$H). $^{13}$C NMR (DMSO-d$_6$): δ ppm 38.53 (C-1), 18.31 (C-2), 37.42 (C-3), 46.53 (C-4), 45.19 (C-5), 55.6 (C-6), 121.25 (C-7), 135.65 (C-8), 51.30 (C-9), 34.65 (C-10), 22.75 (C-11), 27.88 (C-12), 145.34 (C-13), 122.55 (C-14), 34.98 (C-15), 21.11 (C-16), 21.77 (C-17), 184.00 (C-18), 17.00 (C-19), 15.11 (C-20). MS (EI): m/z 300 (80%) [M$^+$]. Anal. Calculated for C$_{20}$H$_{28}$O$_2$ (300.43): Calculated C, 79.96; H, 9.39. Found C, 79.86; H, 9.28.

Example 4

Synthesis of Compounds 4a-4c

As further reflected in FIG. 1, a mixture of lactone compound 2 (58.8 mg, 0.196 mmol) and phenol, thiophenol, or aniline (0.2 mmol) in dry dioxane (10 ml) was heated to reflux for one hour with stirring. The reaction mixture was then evaporated to dryness. The resulting solid was dissolved in methylene chloride, washed first with sodium carbonate solution (1 ml, 5%) and then with water, and then dried over anhydrous magnesium sulfate. The solvent was evaporated to dryness under reduced pressure, and the precipitate was recrystallized from methylacetate/petroleum ether, producing the corresponding 2-hydroxy-derivative compound 4a, 4b, or 4c, respectively.

Example 5

Analysis of Compound 4a
(Phenyl-2-hydroxy-abieta-7,13-dien-18-oate)

Yield 90%, mp. 197-199° C., [α]$_D^{25}$=+95 (c 1, MeOH). IR (KBr, cm$^{-1}$): 3581 (OH), 3045 (CH-aromat), 2921 (CH-aliph), 1738 (C=O), 1651 (C=C). $^1$H NMR (DMSO-d6): 0.86 (s, 3H, CH$_3$, C-20), 1.20 (s, 6H, 2CH$_3$, C-16&17), 1.28 (s, 3H, CH$_3$, C-19), 1.37 (t, 2H, CH$_2$, $^1$H), 1.45 (t, 2H, CH$_2$, $^3$H), 1.67 (t, 2H, CH$_2$, $^{11}$H), 1.74 (m, 1H, CH, $^{15}$H), 1.93 (d, CH$_2$, 2H, $^6$H), 1.99 (t, CH$_2$, 2H, $^{12}$H), 2.03 (t, 1H, CH, $^9$H), 2.28 (m, eq-1H, CH, $^2$H), 2.50 (t, 1H, CH, $^5$H), 3.54 (s, 1H, OH, C-2), 5.39 (m, 1H, $^7$H), 5.79 (s, 1H, $^{14}$H), 7.29-7.49 (m, 5H, Ar—H). $^{13}$C NMR (DMSO-d6): δ ppm 38.38 (C-1), 79.18 (C-2), 37.26 (C-3), 46.34 (C-4), 44.98 (C-5), 25.68 (C-6), 120.57 (C-7), 135.56 (C-8), 51.06 (C-9), 34.56 (C-10), 22.56 (C-11), 27.55 (C-12), 145.18 (C-13), 122.59 (C-14), 34.80 (C-15), 20.91 (C-16), 21.41 (C-17), 172.21 (C-18), 16.72 (C-19), 14.01 (C-20), 157.67, 123.45, 123.45, 130.87, 130.87, 120.10 (Ar—C). MS (EI): m/z 394 (65%) [M$^+$]. Anal. Calculated for C$_{26}$H$_{34}$O$_3$ (394.54): Calculated C, 79.15; H, 8.69. Found C, 79.02; H, 8.58.

Example 6

Analysis of Compound 4b (Phenyl-2-hydroxy-abieta-7,13-dien-18-thioate (4b))

Yield 77%, mp. 237-239° C., [α]$_D^{25}$=+111 (c 1, MeOH). IR (KBr, cm$^{-1}$): 3589 (OH), 3048 (CH-aromat), 2931 (CH-aliph), 1730 (C=O), 1645 (C=C). $^1$H NMR (DMSO-d6): 0.84 (s, $^3$H, CH$_3$, C-20), 1.17 (s, 6H, 2CH$_3$, C-16&17), 1.23 (s, 3H, CH$_3$, C-19), 1.33 (t, 2H, CH$_2$, $^1$H), 1.42 (t, 2H, CH$_2$, $^3$H), 1.62 (t, 2H, CH$_2$, $^{11}$H), 1.71 (m, 1H, CH, $^{15}$H), 1.90 (d, CH$_2$, 2H, $^6$H), 1.96 (t, CH$_2$, 2H, $^{12}$H), 2.00 (t, 1H, CH, $^9$H), 2.24 (m, eq-1H, CH, $^2$H), 2.46 (t, 1H, CH, $^5$H), 3.50 (s, 1H, OH, C-2), 5.36 (m, 1H, $^7$H), 5.74 (s, 1H, $^{14}$H), 7.44-7.88 (m, 5H, Ar—H). $^{13}$C NMR (DMSO-d6): δ ppm 38.22 (C-1), 79.24 (C-2), 37.46 (C-3), 46.67 (C-4), 44.77 (C-5), 25.64 (C-6), 121.65 (C-7), 137.57 (C-8), 50.96 (C-9), 34.98 (C-10), 22.76 (C-11), 27.77 (C-12), 145.88 (C-13), 122.76 (C-14), 34.65 (C-15), 20.44 (C-16), 21.45 (C-17), 194.44 (C-18), 16.72 (C-19), 14.21 (C-20), 142.45, 126.65, 126.65, 129.89, 129.89, 135.10 (Ar—C). MS (EI): m/z 411 (43%) [M$^+$]. Anal. Calculated for C$_{26}$H$_{34}$O$_2$S (410.61): Calculated C, 76.05; H, 8.35; S, 7.81. Found C, 75.95; H, 8.30; S, 7.75.

Example 7

Analysis of Compound 4c
(Phenyl-2-hydroxy-abieta-7,13-dien-18-carboxamide)

Yield 78%, mp. 343-245° C., [α]$_D^{25}$=+167 (c 1, MeOH). IR (KBr, cm$^{-1}$): 3617 (OH & NH), 2927 (CH-aliph), 1746 (C=O), 1658 (C=C). $^1$H NMR (DMSO-d6): 0.84 (s, 3H, CH$_3$, C-20), 1.18 (s, 6H, 2CH$_3$, C-16&17), 1.26 (s, 3H, CH$_3$, C-19), 1.34 (t, 2H, CH$_2$, $^1$H), 1.44 (t, 2H, CH$_2$, $^3$H), 1.64 (t, 2H, CH$_2$, $^{11}$H), 1.73 (m, 1H, CH, $^{15}$H), 1.92 (d, CH$_2$, 2H, $^6$H), 1.95 (t, CH$_2$, 2H, $^{12}$H), 2.00 (t, 1H, CH, $^9$H), 2.34 (m, eq-1H, CH, $^2$H), 2.54 (t, 1H, CH, $^5$H), 3.58 (s, 1H, OH, C-2), 5.39 (m, 1H, $^7$H), 5.80 (s, 1H, $^{14}$H), 7.27-7.41 (m, 5H, Ar—H), 8.97 (s, 1H, NH). $^{13}$C NMR (DMSO-d6): δ ppm 38.56 (C-1), 79.18 (C-2), 37.58 (C-3), 46.90 (C-4), 44.96 (C-5), 25.47 (C-6), 120.69 (C-7), 135.98 (C-8), 51.06 (C-9), 34.65 (C-10), 22.45 (C-11), 27.78 (C-12), 145.67 (C-13), 122.78 (C-14), 34.97 (C-15), 20.54 (C-16), 21.56 (C-17), 172.89 (C-18), 16.66 (C-19), 14.01 (C-20), 139.76, 118.77, 118.77, 128.01, 128.01, 123.09 (Ar—C). MS (EI): m/z 393 (80%) [M$^+$]. Anal. Calculated for C$_{26}$H$_{35}$NO$_2$ (393.56): Calculated C, 79.35; H, 8.96; N, 3.56. Found C, 79.24; H, 8.90; N, 3.50.

Example 8

Synthesis of Compounds 5a-c

As further reflected in FIG. 1, a mixture of lactone compound 3 (58.8 mg, 0.196 mmol) and phenol, thiophenol, or aniline (0.2 mmol) in dry dioxane (10 ml) was heated to reflux for one hour, with stirring. The reaction mixture was evaporated to dryness. The resulting solid was then dissolved in methylene chloride, washed first with sodium carbonate solution (1 ml, 5%) and then with water, and then dried over anhydrous magnesium sulfate. The solvent was evaporated under reduced pressure to dryness, and the precipitate was recrystallized from methylacetate/petroleum ether to produce the corresponding 6-hydroxy-derivative 5a, 5b, or 5c, respectively.

Example 9

Analysis of Compound 5a
(Phenyl-6-hydroxy-abieta-7,13-dien-18-oate)

Yield 96%, mp. 278-280° C., $[\alpha]_D^{25}$=+129 (c 1, MeOH). IR (KBr, cm$^{-1}$): 3588 (OH), 3048 (CH-aromat), 2934 (CH-aliph), 1741 (C=O), 1658 (C=C). $^1$H NMR (DMSO-d$_6$): 0.87 (s, 3H, CH$_3$, C-20), 1.20 (s, 6H, 2CH$_3$, C-16&17), 1.24 (m, 2H, CH$_2$, $^2$H), 1.30 (s, 3H, CH$_3$, C-19), 1.41 (t, 2H, CH$_2$, $^1$H), 1.46 (t, 2H, CH$_2$, $^3$H), 1.65 (t, 2H, CH$_2$, $^{11}$H), 1.76 (m, 1H, CH, $^{15}$H), 1.97 (t, CH$_2$, 2H, $^{12}$H), 2.02 (t, 1H, CH, $^9$H), 2.32 (m, eq-1H, CH, $^6$H), 2.52 (t, 1H, CH, $^5$H), 3.89 (s, 1H, OH, C-6), 5.42 (m, 1H, $^7$H), 5.83 (s, 1H, $^{14}$H) 7.27-7.47 (m, 5H, Ar—H). $^{13}$C NMR (DMSO-d$_6$): δ ppm 38.65 (C-1), 18.43 (C-2), 37.66 (C-3), 46.76 (C-4), 45.43 (C-5), 80.86 (C-6), 121.90 (C-7), 135.86 (C-8), 51.75 (C-9), 34.89 (C-10), 22.09 (C-11), 27.98 (C-12), 145.77 (C-13), 122.85 (C-14), 34.90 (C-15), 21.32 (C-16), 21.80 (C-17), 175.11 (C-18), 17.32 (C-19), 15.09 (C-20) 157.54, 123.55, 123.55, 131.12, 131.12, 121.11 (Ar—C). MS (EI): m/z 394 (79%) [M$^+$]. Anal. Calculated for C$_{26}$H$_{34}$O$_3$ (394.54): Calculated C, 79.02; H, 8.60. Found C, 79.15; H, 8.69.

Example 10

Analysis of Compound 5b
(Phenyl-6-hydroxy-abieta-7,13-dien-18-thioate)

Yield 80%, mp. 263° C., $[\alpha]_D^{25}$=+104 (c 1, MeOH). IR (KBr, cm$^{-1}$): 3580 (OH), 3044 (CH-aromat), 2939 (CH-aliph), 1744 (C=O), 1654 (C=C). $^1$H NMR (DMSO-d$_6$): 0.85 (s, 3H, CH$_3$, C-20), 1.18 (s, 6H, 2CH$_3$, C-16&17), 1.21 (m, 2H, CH$_2$, $^2$H), 1.27 (s, 3H, CH$_3$, C-19), 1.38 (t, 2H, CH$_2$, $^1$H), 1.43 (t, 2H, CH$_2$, $^3$H), 1.62 (t, 2H, CH$_2$, $^{11}$H), 1.73 (m, 1H, CH, $^{15}$H), 1.94 (t, CH$_2$, 2H, $^{12}$H), 2.02 (t, 1H, CH, $^9$H), 2.29 (m, eq-1H, CH, $^6$H), 2.48 (t, 1H, CH, $^5$H), 3.83 (s, 1H, OH, C-6), 5.39 (m, 1H, $^7$H), 5.79 (s, 1H, $^{14}$H) 7.46-7.84 (m, 5H, Ar—H). $^{13}$C NMR (DMSO-d$_6$): δ ppm 38.47 (C-1), 18.47 (C-2), 37.21 (C-3), 46.86 (C-4), 45.97 (C-5), 80.96 (C-6), 121.73 (C-7), 135.64 (C-8), 51.76 (C-9), 34.42 (C-10), 22.54 (C-11), 27.75 (C-12), 145.63 (C-13), 122.21 (C-14), 34.53 (C-15), 21.65 (C-16), 21.43 (C-17), 195.19 (C-18), 17.54 (C-19), 15.32 (C-20) 142.46, 126.66, 126.66, 130.01, 130.01, 135.77 (Ar—C). MS (EI): m/z 410 (70%) [M$^+$]. Anal. Calculated for C$_{26}$H$_{34}$O$_2$S (410.61): Calculated C, 76.05; H, 8.35; S, 7.81. Found C, 75.98; H, 8.31; S, 7.76.

Example 11

Analysis of Compound 5c
(Phenyl-6-hydroxy-abieta-7,13-dien-18-carboxamide)

Yield 78%, mp. 343° C., $[\alpha]_D^{25}$=+167 (c 1, MeOH). IR (KBr, cm$^{-1}$): 3632 (OH & NH), 2941 (CH-aliph), 1750 (C=O), 1661 (C=C). $^1$H NMR (DMSO-d$_6$): 0.88 (s, 3H, CH$_3$, C-20), 1.18 (s, 6H, 2CH$_3$, C-16&17), 1.21 (m, 2H, CH$_2$, $^2$H), 1.37 (s, 3H, CH$_3$, C-19), 1.39 (t, 2H, CH$_2$, $^1$H), 1.45 (t, 2H, CH$_2$, $^3$H), 1.64 (t, 2H, CH$_2$, $^{11}$H), 1.74 (m, 1H, CH, $^{15}$H), 1.97 (t, CH$_2$, 2H, $^{12}$H), 2.00 (t, 1H, CH, $^9$H), 2.58 (m, eq-1H, CH, $^6$H), 2.55 (t, 1H, CH, $^5$H), 3.94 (s, 1H, OH, C-6), 5.46 (m, 1H, $^7$H), 5.86 (s, 1H, $^{14}$H)), 7.31-7.58 (m, 5H, Ar—H), 8.55 (s, 1H, NH). $^{13}$C NMR (DMSO-d$_6$): δ ppm 38.89 (C-1), 18.48 (C-2), 37.68 (C-3), 46.76 (C-4), 45.85 (C-5), 80.67 (C-6), 121.96 (C-7), 135.86 (C-8), 51.55 (C-9), 34.99 (C-10), 22.39 (C-11), 27.94 (C-12), 145.67 (C-13), 122.83 (C-14), 34.9870 (C-15), 21.65 (C-16), 21.34 (C-17), 175.56 (C-18), 17.78 (C-19), 15.90 (C-20), 139.88, 118.66, 118.66, 128.23, 128.23, 123.55 (Ar—C). MS (EI): m/z 393 (100%) [M$^+$]. Anal. Calculated for C$_{26}$H$_{35}$NO$_2$ (393.56): Calculated C, 79.35; H, 8.96; N, 3.56. Found C, 79.05; H, 8.90; N, 3.48.

All of the new derivative compounds 2, 3, 4a-4c, and 5a-5c demonstrate potent 5α-reductase inhibitor activity, both in vitro and in vivo. The compounds, in descending potency of 5α-Reductase inhibitor activity, are in the following order: 4c, 4a, 4b, 2, 5c, 5a, 5b, and 3. All compounds demonstrated higher potency than the reference standards.

All new compounds 2, 3, 4a-4c, and 5a-5c also were screened for anti-tumor activity with regard to two prostate cancer cell lines, namely, LNCaP and PC-3. All compounds demonstrated potent anti-proliferative activities against both cell lines, compared to abietic acid and to known anti-tumor agents finasteride (used to block 5α-reductase in men with enlarged prostate) and anastrozole (a nonsteroidal aromatase inhibitor that decreases estrogen production and is used to treat breast cancer in women after menopause). The compounds, in descending anti-proliferative activity, were again in the following order: 4c, 4a, 4b, 2, 5c, 5a, 5b, and 3. Each of these compounds again outperformed the known treating agents used for comparison in the testing.

Example 12

In Vitro 5α-Reductase Inhibitors Activities
Enzymatic Assay

A homogenate of the ventral prostate gland of male Sprague-Dawley rats was prepared, and testosterone 5α-reductase inhibition was measured using the methods previously reported in Iwai, A., et al., "Spectrophotometric Method for the Assay of Steroid 5α-reductase activity of rat liver and prostate microsomes", *Analytical Sciences* 2013, 29: 455-459. Both the type 1 and the type 2 isozymes are present in the ventral prostate of the rat. In the assay, rat prostate extracts were used in a neutral pH buffer, and both isozymes were assayed.

The ventral prostate glands were excised and minced with a pair of scissors. The 20 w/v % homogenates were prepared with a glass-glass homogenizer in medium A (sucrose 0.32 M, dithiothreitol 0.1 mM, and sodium phosphate 20 mM, pH 6.5). The homogenate was filtered with surgical gauze and then centrifuged at 3000×g for 10 min. The pellets were suspended in medium A at a protein concentration of 20 mg/ml by triturating sequentially through an 18-gauge needle, and then a 20-gauge needle.

To 40 μl of the enzyme suspension, 10 μl of test sample in ethanol or ethanol alone and a mixture containing 0.525 ml of reaction solution consisting of dithiothreitol 1 mM, sodium phosphate 40 mM, pH 6.5, NADPH 5×10$^{-5}$ M, and [1,2,6,7-$^3$H]testosterone 2.2×10$^{-9}$ M were added. The assay mixture was incubated at 37° C. for 30 min. The reaction was stopped by the addition of 1 ml of ethyl acetate, and 50 μl of the upper phase was separated on a silica gel plate in the developing solvent system of ethyl acetate/cyclohexane, at a ratio of 1:1. The zones corresponding to the testosterone and 5α-dihydrotestosterone were cut into fragments. Each fragment was added to 5 ml of Aquasol-2 and counted with a liquid scintillation counter to determine $^3$H radioactivity.

The inhibitory activity of each test sample was calculated as follows:

Rate of enzyme reaction $(R,\%) = D/(T+D) \times 100$

Inhibitory activity $(\%) = (1 - R_{sample}/R_{control}) \times 100$ where D and T are the $^3$H radioactivity recovered. The results are reported in Table 1, and reflected in FIG. 2.

TABLE 1

IC$_{50}$ Values of compounds tested on rat prostate testosterone 5α-reductase activity

| Compound | IC$_{50}$, μM |
|---|---|
| Ethanol | 0.000 ± 0.000 |
| Abietic acid | 56 ± 22 |
| Finasteride | 0.06 ± 0.0012 |
| Anastrozole | 11.23 ± 0.023 |
| 2 | 0.00034 ± 0.00006 |
| 3 | 0.00091 ± 0.00007 |
| 4a | 0.00022 ± 0.00003 |
| 4b | 0.00029 ± 0.00001 |
| 4c | 0.00019 ± 0.00002 |
| 5a | 0.00074 ± 0.00006 |
| 5b | 0.00088 ± 0.00007 |
| 5c | 0.00068 ± 0.00008 |

Values were calculated from the mean values of data from three separate experiments.
All results are significant different from control values at p ≤ 0.005.
All results are significantly different from reference standard values at p ≤ 0.005.

Figure 2:
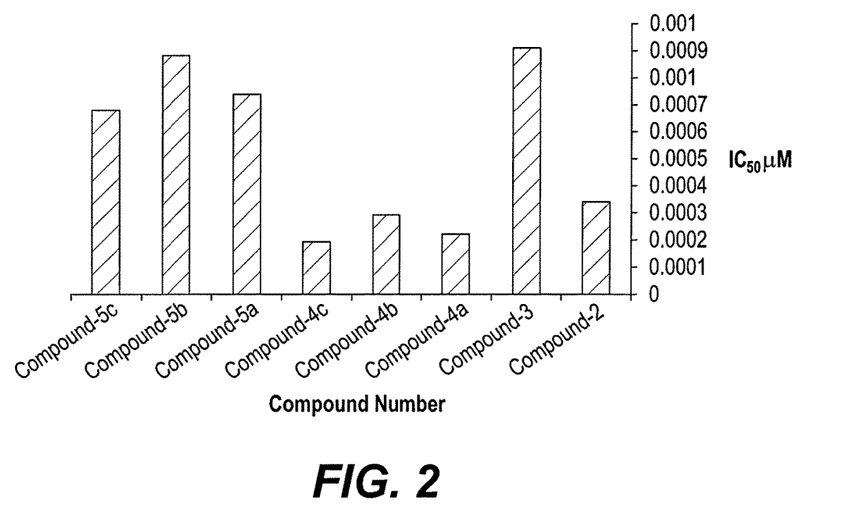
FIG. 2 is a chart reflecting the $IC_{50}$ values of the compounds produced according to the scheme of FIG. 1, regarding in vitro inhibitory effect on rat 5α-reductase activity.

As is evident from Table 1 and FIG. 2, the IC$_{50}$ values (concentrations providing 50% inhibition) for each of the compounds 2, 3, 4a-c, and 5a-c demonstrate substantially higher, and statistically, significantly higher inhibition of 5α-reductase activity compared to the standard known agents, i.e., abietic acid, finasteride, and anastrozole.

Example 13

In Vivo 5α-Reductase Inhibitor Activities Biological Assay

Animals were obtained from the animal house colony of the National Research Center, Cairo, Egypt. All animals were allowed free access to water and were kept on a constant standard diet. Twenty three groups, each with 12 male Sprague-Dawley rats each at the age of three days postnatal, were treated subcutaneously with the 5α-reductase inhibitor tested compound or the reference standard. The tested compounds were dissolved in 5% Tween 80 in water. The vehicle was used for both standard and negative control group, beginning on the postnatal third day until the age of seven weeks. Eleven groups were used for measuring activity levels, including one group as the positive control (anastrozole) and a second group as the negative control. The remaining 9 groups were tested with abietic acid and the newly synthesized compounds 2, 3, 4a-4c, and 5a-5c.

After sacrificing, blood was withdrawn for determining levels of testosterone and dihydrotestosterone (DHT), as reported in S. Shiraishi et al., "Simultaneous measurement of serum testosterone and dihydrotestosterone by liquid chromatography-tandem mass spectrometry", *Clinical Chemistry* 2008, 54(11): 1855-1863. Moreover, intraprostatic concentrations of testosterone and DHT were determined as reported in E. Disalle et al., "Hormonal effects of turosteride, a 5 alpha-reductase inhibitor, in the rat", *J. Steroid Biochem. Molec. Biol.*, 1993, 46: 549-555. The biological experiments were performed according to official standards.

Figure 3:
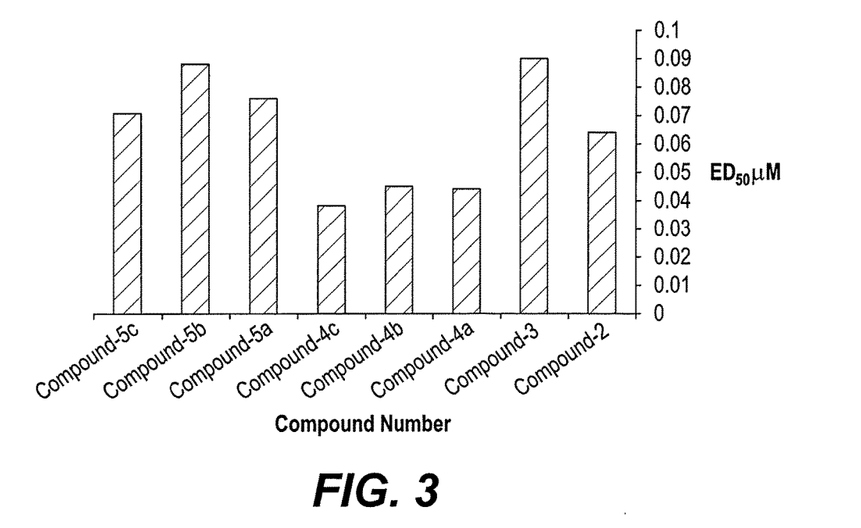
FIG. 3 is a chart of the $ED_{50}$ values of the compounds produced according to the scheme of FIG. 1, regarding in vivo inhibitory effect on rat 5α-reductase activity.

The results are reported in Table 2, and also reflected in FIG. 3.

TABLE 2

ED$_{50}$ of the 5α-reductase inhibitors activities of the studied compounds

| Compound | ED$_{50}$ μM |
|---|---|
| Vehicle (control) | 0.000 ± 0.000 |
| Abietic acid | 8.8 ± 0.087 |
| Finasteride | 0.17 ± 0.0079 |
| Anastrozole | 1.09 ± 0.0034 |
| 2 | 0.064 ± 0.00076 |
| 3 | 0.090 ± 0.00088 |
| 4a | 0.044 ± 0.00065 |
| 4b | 0.045 ± 0.00057 |
| 4c | 0.038 ± 0.00045 |
| 5a | 0.076 ± 0.00089 |
| 5b | 0.088 ± 0.00089 |
| 5c | 0.071 ± 0.00074 |

Values calculated from the mean values of data from three separate experiments.
All results significantly different from control values at p ≤ 0.005.
All results significantly different from reference standard values at p ≤ 0.005.

As reflected in Table 2 and FIG. 3, the ED$_{50}$ values (concentrations providing effective dose for 50% of the test population) for each of the compounds 2, 3, 4a-c, and 5a-c demonstrate substantially higher, and statistically, significantly higher potency as 5α-reductase inhibitors compared to the standard known agents, i.e., abietic acid, finasteride, and anastrozole. These results were also statistically significant compared to the control results.

Example 14

Anti-Prostate Cancer Screening Anti-Androgenic Bioassay in Human Prostate Cancer Cells Human prostate cancer cell lines LNCaP and PC-3 were maintained in RPMI 1640 medium and DMEM medium, respectively. Both media were supplemented with penicillin (25 units/mL), streptomycin (25 μg/mL), and 10% fetal calf serum. For the androgen receptor transactivation assay, an androgen-dependent reporter gene transcription test was employed as the primary screening for potential anti-androgen identification. This assay was first performed in LNCaP cells, which express a clinically relevant mutant AR.

Once anti-androgenic activity was detected in the LNCaP AR transactivation assay, compounds were re-examined for their potential activity against wild type AR. Wild type AR transactivation assay was performed in PC-3 host cells, which lack an endogenous, functional AR.

Cells were plated in 24-well tissue culture dishes for 24 hours (PC-3 cells) or 48 hours (LNCaP cells) prior to transfection. Subsequently, LNCaP cells were transfected with a reporter gene, MMTV-luciferase, which contains MMTV-LTR promoter and androgen receptor binding element, and PRL-SV40, which served as an internal control for transfection efficiency. PC-3 cells were transfected with a wild type AR expression plasmid, pSG5AR, in addition to the aforementioned MMTV-luciferase reporter gene and PRL-SV40 internal control. SuperFect (Qiagen, Chatsworth, Calif.) was employed as the transfection reagent following manufacturer's recommendations.

At the end of a 5-hour transfection period, the medium was changed to DMEM or RPMI 1640 medium, supplemented with 10% charcoal dextran-stripped (that is, androgen-depleted) serum. After 24 h, the cells were treated with 1 nM of DHT and/or test compounds at the designated concentration for another 24 h. The cells were harvested for luciferase activity assay using the Dual Luciferase Assay System (Promega, Madison, Wis.).

The derived data were expressed as relative luciferase activity normalized to the internal luciferase control. Cells cultured in medium containing DHT (androgen), as a positive control, induced a marked reporter gene expression. Test compounds capable of significantly suppressing this DHT induced reporter gene expression were identified as potential anti-androgens. The results are reported in Table 3, and reflected in FIGS. 4 and 5.

TABLE 3

Anti-tumor activity against prostate cancer cell lines

| Compound | LNCaP $IC_{50}$ nM | PC3 $IC_{50}$ nM |
| --- | --- | --- |
| Control | 0.00 ± 0.00 | 0.00 ± 0.00 |
| Finasteride | (>100,000) | (>100,000) |
| 2 | 4.22 ± 0.03 | 45.66 ± 1.09 |
| 3 | 9.08 ± 0.08 | 112.13 ± 3.7 |
| 4a | 3.24 ± 0.04 | 18.16 ± 11 |
| 4b | 3.58 ± 0.02 | 26.45 ± 1.8 |
| 4c | 2.33 ± 0.05 | 11.14 ± 0.09 |
| 5a | 6.21 ± 0.04 | 71.22 ± 3.6 |
| 5b | 7.80 ± 0.09 | 83.48 ± 2.3 |
| 5c | 5.78 ± 0.03 | 66.18 ± 2.3 |

Values calculated from the mean values of data from three separate experiments.
All results significantly different from control values at $p \leq 0.005$.
All results significantly different from reference standard values at $p \leq 0.005$.

Figure 4:
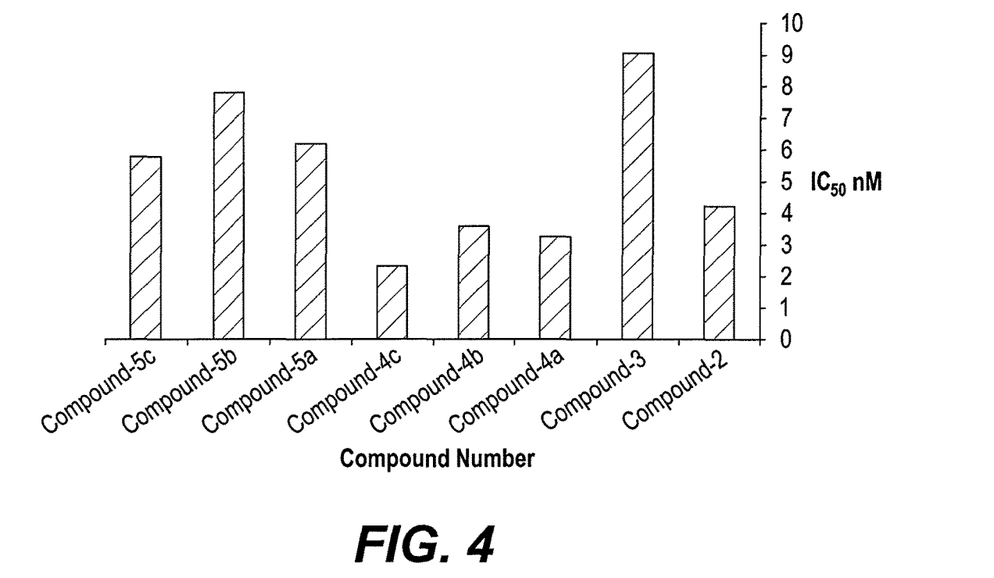
FIG. 4 is a chart of the $IC_{50}$ values of the compounds produced according to the scheme of FIG. 1, regarding anti-tumor activity against prostate cancer cell line LNCaP.
Figure 5:
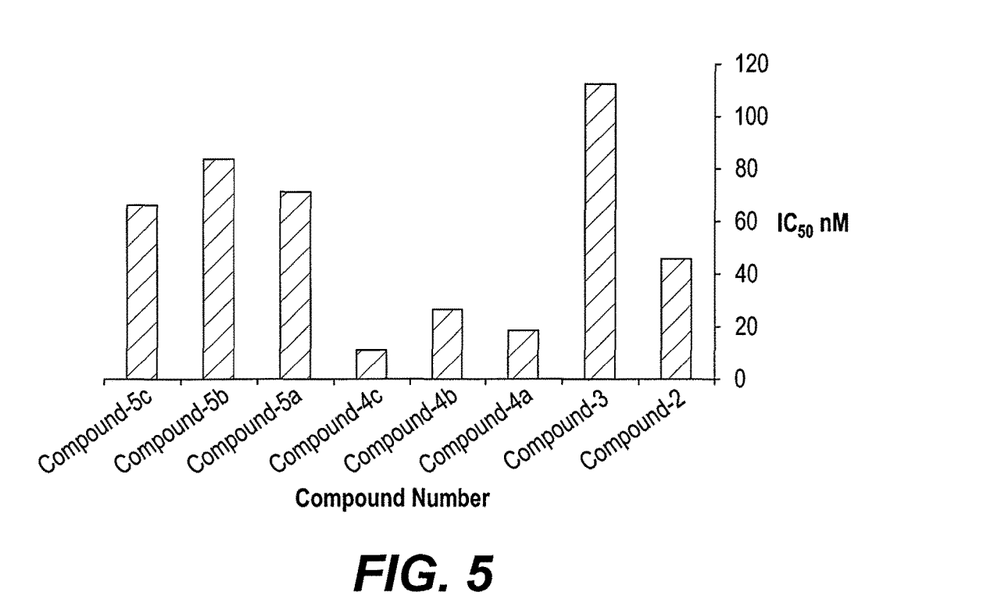
FIG. 5 is a chart of the $IC_{50}$ values of the compounds produced according to the scheme of FIG. 1, regarding anti-tumor activity against prostate cancer cell line PC3.

As reflected in Table 3 and FIGS. 4 and 5, the $IC_{50}$ values demonstrate substantial activity in inhibiting prostate cancer cells for each of the new compounds, 2, 3, 4a-4c, and 5a-5c.

The relationship between the chemical structure of the newly synthesized derivatives and their biological activity as 5α-reductase inhibitors and anti-tumor agents lead to several conclusions. (1) The fusion of the lactone ring system onto ring A of the abietic acid scaffold seems to play a big part in providing both potent 5α-reductase inhibition, and anti-tumor activity at least in PC3 and LNCaP cell lines. (2) The (18→2) lactone (compound 2) provides more 5α-reductase inhibition and anti-tumor activity than the (18→6) lactone (compound 3). (3) The hydroxyl group in the C2 position or the C6 position of the abietic acid frame apparently helps provide sharp increases in 5α-reductase inhibition and anti-tumor activity as compared to the lactone compounds, probably due at least in part to the higher lipophilic character provided by the hydroxyl groups. (4) Compounds with the hydroxyl group located at the C2 position provide more potent 5α-reductase inhibition and anti-tumor activity than compounds with the hydroxyl group located at the C6 position. (5) Regarding modifications at the X position in the molecule in compounds 4a-4c and 5a-5c, the anilide compounds 4c and 5c provide greater 5α-reductase inhibition and anti-tumor activity than the phenolic ester compounds 4a and 5a, which, in turn, were more potent than the thio ester compounds 4b and 5b, respectively. Each of these compounds 4a-4c and 5a-5c demonstrated significant anti-tumor activity, as well as 5α-reductase inhibition. These compounds seem to be useful as anti-tumor agents.

It is to be understood that the abietic acid derivatives as anti-tumor agents for two prostate cell lines is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An abietic acid derivative as an anti-tumor agent, corresponding to a derivative of abietic acid in which the hydroxyl entity (—OH) of the carboxyl entity is replaced by an electronegative substituent, selected from the group consisting of C6H5-O—, C6H5-S—, or C6H5-NH—, and a hydrogen atom on one of the rings is replaced by a hydroxyl (—OH) substituent, the derivative having the formula:

wherein X is O, S, or NH.

2. The abietic acid derivative according to claim 1, having the formula:

wherein X is O.

3. The abietic acid derivative according to claim 1, having the formula:

wherein X is S.

4. The abietic acid derivative according to claim 1, having the formula:

wherein X is NH.

5. The abietic acid derivative according to claim 1, having the formula:

wherein X is O.

6. The abietic acid derivative according to claim 1, having the formula:

wherein X is S.

7. The abietic acid derivative according to claim 1, having the formula:

wherein X is NH.

8. A method of making an abietic acid derivative according to claim 1, comprising the steps of:

reacting abietic acid and ethyl chloroformate in a mixture of tetrahydrofuran and dimethylsulfoxide in the presence of trimethylamine to prepare a mixture of lactones having the formulas:

and separating the lactones of formula 2 and formula 3 by fractionating on a medium pressure chromatography column; and separately reacting the lactones of formula 2 and formula 3 with an electronegative compound selected from the group consisting of phenol, thiophenol, and aniline to obtain a desired derivative.

9. The method of making an abietic acid derivative according to claim 8, wherein said step of separately reacting the lactones of formula 2 and formula 3 comprises reacting the lactone of formula 2 with an electronegative compound selected from the group consisting of phenol, thiophenol, and aniline to obtain an abietic acid derivative having the formula:

wherein X is O, S, or NH.

10. The method of making an abietic acid derivative according to claim 8, wherein said step of separately reacting the lactones of formula 2 and formula 3 comprises reacting the lactone of formula 2 with an electronegative compound selected from the group consisting of phenol, thiophenol, and aniline to obtain an abietic acid derivative having the formula:

wherein X is O, S, or NH.

11. A method for achieving an effect in a patient, comprising administering an effective amount of an abietic acid derivative according to claim 1 to the patient, wherein the effect is inhibiting testosterone 5α-reductase activity or inhibiting growth of a prostate cancer tumor.

12. The method for achieving an effect in a patient according to claim 11, wherein the abietic acid derivative is a compound having the formula:

wherein X is O, S, or NH.

13. The method for achieving an effect in a patient according to claim 11, wherein the abietic acid derivative is a compound having the formula:

wherein X is O, S, or NH.

* * * * *